United States Patent
Von Knebel Doeberitz et al.

(10) Patent No.: US 6,709,832 B1
(45) Date of Patent: Mar. 23, 2004

(54) METHOD OF EARLY DIAGNOSIS OF CARCINOMAS

(75) Inventors: Magnus Von Knebel Doeberitz, Rainweg 93, D 69118 Heidelberg (DE); Dimitry Spitkovsky, Frechen (DE)

(73) Assignees: Magnus Von Knebel Doeberitz, Heidelberg (DE); Deutsches Krebsforschungszentrum, Heidelberg (DE)

( * ) Notice: Subject to any disclaimer, the term of this patent is extended or adjusted under 35 U.S.C. 154(b) by 0 days.

(21) Appl. No.: 09/743,103

(22) PCT Filed: Jul. 1, 1999

(86) PCT No.: PCT/DE99/02094

§ 371 (c)(1),
(2), (4) Date: Aug. 3, 2001

(87) PCT Pub. No.: WO00/01845

PCT Pub. Date: Jan. 13, 2000

(30) Foreign Application Priority Data

Jul. 1, 1998 (DE) .......................... 198 29 473

(51) Int. Cl.[7] .......................... C17Q 1/68; G01N 33/53; G01N 33/567; G01N 33/574; G01N 33/555

(52) U.S. Cl. .......................... 435/7.23; 435/6; 435/7.1; 435/7.2; 435/7.24; 436/63; 436/64; 436/501; 436/503; 530/350; 530/385; 530/386; 530/388.1; 530/388.8; 530/388.85

(58) Field of Search .............................. 435/6, 7.1, 7.2, 435/7.23, 7.24; 436/63, 64, 501, 503; 530/388.1, 388.8, 388.85, 350, 385, 386

(56) References Cited

U.S. PATENT DOCUMENTS

| | | | |
|---|---|---|---|
| 5,976,799 A | 11/1999 | O'Brien et al. | ................ 435/6 |
| 6,287,775 B1 | 9/2001 | O'Brien et al. | ................ 435/6 |

FOREIGN PATENT DOCUMENTS

| | | |
|---|---|---|
| WO | WO 94/09135 | 4/1994 |
| WO | WO 94/12881 | 6/1994 |
| WO | WO 94/17414 | 8/1994 |

OTHER PUBLICATIONS

Geradts, Joseph, et al., *Cancer Research*, Immunohistochemical Detection of the Cyclin–dependent Kinase Inhibitor 2/Multiple Tumor Suppressor Gene 1 (CDKN2/MTS1) Product p16INK4A in Archival Human Solid Tumors: Correlation with Retinoblastoma Protein Expression (1995) 55 (6006–6011).

Hirama, Toshiyasu, et al., *Modern Pathology*, (1996), 9/1 (26–31), p16 (CDKN2/Cyclin–dependent Kinase–4 Inhibitor/Multiple Tumor Suppressor–1) Gene Is Not Altered in Uterine Cervical Carcinomas or Cell Lines.

Kelley, Michael J., et al., *International Journal of Cancer*, (1995) 63/2 (226–230), CDKN2 in HPV–positive and HPV–negative cervical–carcinoma cell lines.

Kim, et al., *Experimental and Molecular Medicine*, (Jun. 30, 1998) 30/2 (109–113), Alterations of CDKN2 (MTS1/p16(INK4A) gene in paraffin–embedded tumor tissues of human stomach, lung, cervix and liver cancers.

Kim, et al., *Gynecologic Oncology*, (1998) 71/1 (38–45), Underexpression of cyclin–dependent kinase (CDK) inhibitors in cervical carcinoma, (concludes that the CDK inhibitors (including p16) are significantly decreased in cervical carcinoma tissues.

Kim, et al., *Gynecologic Oncology*, (1998) 70 (75–79), Absence of p15INK4B and p16INK4A Gene Alterations in Primary Cervical Carcinoma Tissues and Cell Lines with Human Papillomavirus Infection.

Klaes, Ruediger, et al., *Int. J. Cancer*, (2001) 92 (276–284), Overexpression of p16INK4A As A Specific Marker For Dysplastic And Neoplastic Epithelial Cells Of The Cervix Uteri.

Milde–Langosch, et al., *Int. J. Cancer*, (1988) 79(1) (61–65), p16/MTS1 inactivation in ovarian carcinomas: high frequency of reduced protein expression associated with hyper–methylation or mutation in endometrioid and mucinous tumors.

Milde–Langosch, et al., *Virchows Archiv*, (1999) 434/1 (23–28), P16/MTS1 and pRB expression in endometrial carcinomas.

Nuovo, et al., *Proceedings of the National Academy of Sciences of the United States of America* (Oct. 26, 1999) 96/22 (12754–12759), In situ detection of the hypermethylation–induced inactivation of the p16 gene as an early event in oncogenesis.

Sano, Takaaki, et al., *Pathology International* (1998) 48 (580–585); Immunohistochemical overexpression of p16 protein associated with intact retinoblastoma protein expression in cervical cancer and cervical intraepithelial neoplasia.

Sano, Takaaki, et al., *American Journal of Pathology*, (1998) 153/6 (1741–1448), Expression Status of p16 Protein Is Associated with Huma Papillomavirus Oncogenic Potentila in Cervical and Genital Lesions.

Shigemasa, K., et al., *J. Soc. Gynecol Invest*, (1997) 4/2 (95–102), p16 Overexpression: A Potential Early Indicator of Transformation in Ovarian Carcinoma.

Shim, et al., *Clinical Cancer Research*, (1998) 4/12 (3045–3050), Profiling of differentially expressed genes in human primary cervical cancer by complementary DNA expression array.

(List continued on next page.)

*Primary Examiner*—Alana M. Harris
(74) *Attorney, Agent, or Firm*—Albert P. Halluin; Viola T. Kung; Howrey, Simon, Arnold & White, LLP

(57) ABSTRACT

The present invention relates to a method for the early diagnosis of carcinomas and their preliminary stages, which comprises determining the overexpression of a cell cycle regulatory protein in a body sample. The invention also provides a kit usable for this purpose.

5 Claims, 2 Drawing Sheets

OTHER PUBLICATIONS

Tam, S.W., et al., *Cancer Res.*, (1994) 54/22 (5816–5820), Differential expresionand cell cycle regulation of the cyclin–dependent kinase 4 inhibitor p16INK4.

Wong, Y.F., et al., *Gynecol Oncol* (1997) 65/2 (319–324), p16INK4 and p15INK4B alterations in primary gynecologic malignancy.

Wong, Y.F., et al., *Cancer Letters*, (1999) 136/2 (231–235), Methylation of p16(INK4A) in primary gynecologic malignancy.

Li et al. Zhonghua Zhongliu Zazhi 19/4:306–308, Jul. 1997.*

Gemma et al. (International Journal of Cancer 68:605–611, 1996.*

Su et al. Journal of China Medical University 27/4:394–396, Aug. 1998.*

Balazs et al. Genes, Chromosomes and Cancer 19 :84–89, 1997.*

Perry et al. Journal of Neuropathology and Experimental Neurology 56/9:999–1008, Sep. 1997.*

Shiohara et al. Leukemia 10:1897–1900, 1996.*

Ferrando et al. Hum Genet 97:91–94, 1996.*

Kawamata et al. Cancer 77/3:570–575, Feb. 1996.*

Huang et al. Hua Xi Yi De Da Xue Xue Bao, 23/1:61–64, Mar. 1992.*

Tron et al. American Journal of Pathology, 149/4:1139–1146, Oct. 1996.*

Mugikura et al. Sapporo Med. Journal 60/2:139–148, 1991.*

D.C. Betticher, et al., "Prognostic significance of CCND1 (cyclin D1) overexpression in primary resected non–small–cell–lung cancer," *Br. J. Cancer,* 73(3) 294–300 (1996).

V. Esposito, et al., "Prognostic Role of the Cyclin–dependent Kinase Inhibitor p27 in Non–Small Cell Lung Cancer," abstract XP002912136, Aug. 15, 1997.

M. Kania, et al. "Immunohistochemical Detection of Sex Steroid Receptors, Cyclins, and Cyclin–Dependent Kinases in the Normal and Neoplastic Squamous Epithelia of the Uterine Cervix", *Cancer,* 82(9):1709–1719 (1998).

Y. Murakami and T, Sekiya, "Accumulation of genetic alterations and their significance in each primary human cancer and cell line," *Mutation Research, 400*(1–2):421–437 (1998).

G.E. Nichols, et al., "Cyclin D1 Gene Expression in Human Cervical Neoplasia," *Modern Pathology, 9*(4): 418–425 (1996).

I. Orlow, et al., "Cyclin–dependent Kinase Inhibitor p57$^{KIP2}$ in Soft Tissue Scarcomas and Wilms' Tumors," *Cancer Research, 56*(6):1219–1221 (1996).

I.E. Shcauer, et al., "Cyclin D1 overexpression vs. retinoblastoma inactivation: Implications for growth control evasion in non–small cell lung cancer," *Proc. Natl. Acad. Sci., 91*(16):7827–7831 (1994).

T. Zhang, et al., "Concurrent Overexpression of Cyclin D1 and Cyclin–dependent Kinase 4 (Cdk4) in Intestinal Adenomas from Multiple Intestinal Neoplasia (Min) Mice and Human Familial Adenomatous Polyposis Patients," *Cancer Res.* 57(1) 169–175 (1997).

* cited by examiner

NIH3T3 co   E7

← p19

← cdk6

METHOD OF EARLY DIAGNOSIS OF CARCINOMAS

This application is a National Stage of International Application PCT/DE99/02094, filed Jul. 1, 1999; which claims the priority of DE 198 29 473.5, filed Jul. 1, 1998. The present invention relates to a method for the early diagnosis of carcinomas as well as their preliminary stages, particularly carcinomas of the upper respiratory tract or the anogenital tract.

FIELD OF THE INVENTION

The present invention relates to a method for the early diagnosis of carcinomas as well as their preliminary stages, particularly carcinomas of the upper respiratory tract or the anogenital tract.

BACKGROUND OF THE INVENTION

Preventive programs have been offered for the most differing carcinomas since the middle of the 50ies. Regarding the cervical carcinoma they are based mainly on the morphological and cytological examination of cytosmears of the cervix uteri, what is called the Pap test, which is made on the basis of gynecological routine examinations at regular intervals in women from the $20^{th}$ year on. By means of the morphology of the cells, the smears are divided into various intensity degrees of dysplastic cellular changes. According to Pap I–V, these intensity degrees are referred to as normal, mild dysplasia, fairly serious dysplasia, serious dysplasia and invasive carcinoma, respectively. If the Pap test leads to a striking result, a small biopsy will be taken and subjected to a histopathologic examination, by which the kind and intensity of the dysplasia are determined and classified as cervical intraepithelial neoplasia (CINI–III).

In spite of all preventive programs, the cervical carcinoma which leads to 400,000 new cases per year is the: most frequent carcinoma in women. This is inter alia due to the fact that up to 30% of the Pap test results are false-negative.

Therefore, it is the object of the present invention to provide a method by which cervical carcinomas can be diagnosed early and reliably. In addition, a differentiation should be possible by this method with respect to benign inflammatory or metaplastic changes of dysplastic preneoplasias.

According to the invention, this is achieved by the subject matters defined in the claims.

SUMMARY OF THE INVENTION

The present invention is based on the applicant's insights that cell cycle regulatory proteins are overexpressed in many carcinomas, e.g., carcinomas of the upper respiratory tract or anogenital carcinomas, particularly cervical carcinoma, and preliminary stages of these carcinomas. Examples of the cell cycle regulatory proteins are cyclins. Cyclin-dependent kinases which regulate the cyclins are to be mentioned particularly. Cyclin-dependent kinase inhibitors which, in turn, regulate the cyclin-dependent kinases, are to be mentioned even more particularly. Examples of the cyclin-dependent kinase inhibitors are the proteins p14, p15, p16, p19, p21 and p27. The applicant has found that the intensity of cell cycle regulatory protein overexpression correlates with the degree of cell dysplasia.

DETAILED DESCRIPTION OF THE INVENTION

Figure 1:
FIG. 1 shows the detection of the cdk4 overexpression in HPV16-transformed cervical carcinoma cells CaSki. The indications 4 h, 8 h, 12 h, 24 h refer to the times of cell extract removal. The indication co stands for control while arr indicates the addition of the serum.
Figure 1:
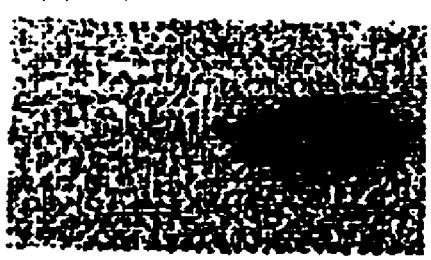

The present invention provides a method for the early diagnosis of carcinomas and their preliminary stages, which comprises determining the overexpression of cell cycle proteins in a body sample.

The expression "carcinomas and their preliminary stages" comprises carcinomas of any kind and origin and preliminary stages thereof. For example, they may be carcinomas of the upper respiratory tract or anogenital carcinomas, particularly the cervical carcinoma. In connection with the latter, its preliminary stages, e.g., cervical intraepithelial neoplasias (CINI–III), carcinomas in situ (CIS), etc., have to be mentioned particularly.

The expression "cell cycle regulatory proteins" comprises cell cycle regulatory proteins of any kind and origin. For example, the proteins may be cyclins. In particular, they may be cyclin-dependent kinases which regulate the cyclins. Examples of the cyclin-dependent kinases are the proteins cdk4 and cdk6. More particularly, they may be cyclin-dependent kinase inhibitors which, in turn, regulate the cyclin-dependent kinases. Examples of cyclin-dependent kinase inhibitors are the proteins p14, p15, p16, p18, p19, p21 and p27, with p16 being preferred.

The expression "body sample" comprises any body samples in which cell cycle regulatory proteins can be detected. Examples of such body samples are blood, smears, sputum, urine, stool, liquor, bile, gastrointestinal secretions, lymph, bone marrow, organ punctates or aspirates and biopsies. In particular, smears and biopsies are indicated when the detection of anogenital carcinomas, e.g., cervical carcinomas, is concerned.

The expression "determining the overexpression of cell cycle regulatory proteins" comprises any methods which are suited for detecting the expression of cell cycle regulatory proteins or their encoding mRNAs and an amplification of the corresponding genes, respectively. In order to determine an overexpression, it is an obvious thing to compare the body sample to be examined with a corresponding body sample which originates from a healthy person. Such a sample can be present in standardized form. The (over) expression of cell cycle regulatory proteins can be detected on a nucleic acid level or protein level. Regarding the detection on a protein level, it is possible to use, e.g., antibodies which are directed against cell cycle regulatory proteins. These antibodies can be used in various methods such as Western blot, ELISA or immunoprecipitation. It may be favorable for the antibodies to be fixed on solid carriers such as test strips or latex particles.

By means of the present invention, it is possible to diagnose carcinomas early, i.e., in their preliminary stages.

A further subject matter of the present invention relates to a kit for carrying out a method according to the invention. Such a kit comprises:

(a) a reagent for detecting the expression of a cell cycle regulatory protein, e.g., an antibody directed against (b) conventional auxiliary agents, such as buffers, carriers, markers, etc., and optionally (c) an agent for control reactions, e.g., a cell cycle regulatory protein, a nucleic acid coding for such a protein and parts thereof, or a preparation of cells, e.g., a tissue section or cells fixed on a slide.

The above statements apply correspondingly to the individual components of the kit. Furthermore, one or several representatives of the individual components may be present.

By means of the present invention, it is possible to diagnose carcinomas early. In particular, preliminary stages of carcinomas can be detected early. It must also be emphasized that it is possible to make a differentiation with respect to benign inflammatory or metaplastic changes of dysplastic preneoplasias. Another characteristic is that the results obtained by a method according to the invention are not subject to a subjective evaluation, therefore, the false-negative results and false-positive results, of a Pap test or of histological preparations can be avoided. In addition, the present invention distinguishes itself by a rapid and simple handling, therefore, it can be used for extensive screening measures, particularly in third-world countries. Thus, the present invention represents an important contribution to today's diagnostics of cancerous diseases.

The invention is explained by the following examples.

EXAMPLES

Example 1

Detection of the Overexpression of p16 in Biopsies of the Cervix Uteri (A) Paraffin sections having a thickness of 3 to 5 $\mu$m were produced from 20 biopsies of the cervix uteri, which comprised all degrees of the dysplastic progression from normal tissue (n=2) via CIN I (n=4), II (n=4), III (n=5) lesions to the invasive carcinoma (n=5). They were deparaffinized in xylene for 2×10 min. and rehydrogenated using ethanol. The antigens were demasked in 10 mM citrate buffer (pH 6.0) in an autoclave at 110° C. for 10 min. Thereafter, the endogenous peroxidases were inactivated using 0.25% $H_2O_2$ in PBS. Following the blocking of unspecific binding sites with horse serum (Vectastain ABC detection kit, Vector Laboratories, Burlingame, Calif., U.S.A.) at room temperature for 20 minutes, the sections were incubated with a p16-specific monoclonal antibody (Neomarkers, Fremont, Calif., U.S.A.) in the presence of 3% fetal calf serum at room temperature for 45 min. For the detection of the p16-antibody binding, a biotinylated secondary antibody (horse anti-mouse IgG, Vectastain kit, see above) was then added for 30 minutes. Thereafter, the bound secondary antibody was detected by means of the reagents and in accordance with the Vectastain kit instructions and a core counterstain was carried out using Mayer's hemalum solution.

It shows that an overexpression of p16 exists in dysplasia cells. It also shows that the intensity of p16 overexpression correlates with the degree of cell dysplasia.

(B) In addition, paraffin sections were prepared from 78 biopsies of the cervix uteri. The biopsies related to normal tissue (n=12), dysplastic lesions of stages CIN I (n=15), II (n=14) and III (n=18) as well as invasive carcinomas (n=19). The paraffin sections were treated as described in (A). The data indicated in Table 1 were obtained.

TABLE 1

| | p 16 expression intensity | | | | |
|---|---|---|---|---|---|
| histology | n = | − | + | ++ | +++ |
| normal | 12 | 9 | 3 | | |
| CIN I | 15 | 10 | 3 | 2 | |
| CIN II | 14 | 1 | 4 | 9 | |
| CIN III | 18 | | | 9 | 9 |
| CxCa | 19 | | | 1 | 18 |
| total | 78 | 20 | 10 | 21 | 27 |

The data of Table 1 show that p16 is overexpressed in cells of dysplasias and invasive carcinomas; the overexpression increases with the degree of dysplasia towards the invasive carcinoma.

(C) Moreover, paraffin sections from 180 biopsies of the cervix uteri were treated as described in (A). In addition, the percentage cell number which reacts with the above-mentioned p16-specific monoclonal antibody was determined. A distinction was also made between HPV-positive and HPV-negative dysplasias and invasive carcinomas, respectively. The data indicated in Table 2 were obtained.

TABLE 2

| Percentage of cells overexpressing p16 | | |
|---|---|---|
| | n | average percentage ± standard deviation |
| CIN I | 32 | 54.9 ± 24.0 |
| HPV-negative | 17 | 54.0 ± 27.2 |
| HPV-positive | 15 | 55.9 ± 21.0 |
| CIN II | 32 | 70.8 ± 18.9 |
| HPV-negative | 14 | 76.0 ± 15.8 |
| HPV-positive | 18 | 66.8 ± 20.5 |
| CIN III | 60 | 92.4 ± 10.2 |
| HPV-negative | 9 | 94.4 ± 7.5 |
| HPV-positive | 51 | 92.1 ± 10.7 |
| Invasive carcinoma | 58 | 97.8 ± 5.2 |
| HPV-negative | 5 | 96.4 ± 8.1 |
| HPV-positive | 53 | 97.9 ± 4.9 |

The data of Table 2 disclose that p16 is overexpressed in both HPV-positive cells and HPV-negative cells of dysplasias and invasive carcinomas. This result is confirmed by controls with normal tissue. The data also show that the percentage of cells reacting with p16 increases with the degree of dysplasia towards the invasive carcinoma.

Example 2

Detection of the Overexpression of Cell Cycle Regulatory Proteins in HPV-transformed Cells (A) Cervical carcinoma cells CaSki which were transformed with HPV16 were cultured in the absence of serum for 72 h. Following the addition of serum, cell extracts were collected at various times, subjected to SDS-PAGE and transferred to PVDF membranes (Du Pont). The expression of cdk4 was determined using polyclonal antiserum (1:1000) from Santa Cruz. Furthermore, the expression of HPV16-E7 protein was determined with a monoclonal antibody against HPV16-E7 (1:50) from Triton. The individual immune responses were detected via peroxidase-linked second antibodies and a chemiluminescence detection system (NEN, Du Pont).

The results show that cdk4 is overexpressed (cf. FIG. 1).

(B) NIH3T3 cells were transformed with HPV16 so as to obtain an expression of HPV16-E7 protein. Cell extracts of the transformed cells were obtained and treated as described in (A). For detecting the expression of cdk6 and p19, respectively, polyclonal antisera (1:1000) from Santa Cruz were used. As far as the detection of the expression of HPV16-E7 protein and the detection of the individual immune responses were concerned, reference was made to the above statements under item (A).

Figure 2:
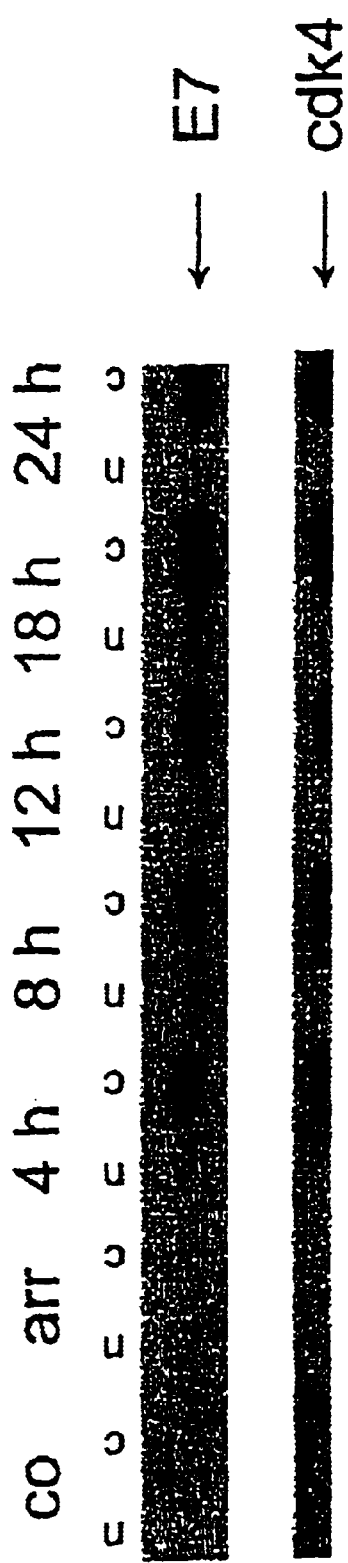
FIG. 2 shows the detection of the overexpression of cdk6 and p19 in HPV16-transformed NIH3T3 cells. The indication co stands for control.

The results show that cdk6 and p19 are overexpressed (cf. FIG. 2).

What is claimed is:

1. A method for detecting cervical carcinomas, cervical intraepithelial neoplasias, or cervical carcinomas in situ, comprising determining the overexpression of cyclin-dependent kinase inhibitor p16 in a human cervical body sample by comparing the expression level of cyclin-dependent kinase inhibitor p16 within said sample to the expression level present in a healthy human cervical body sample.

2. The method according to claim 1, wherein the human cervical body sample is smears, organ punctates, or biopsies.

3. The method according to claim 2, wherein the overexpression is determined by detecting the mRNAs encoding the cell-cycle regulatory protien cyclin-dependent kinase inhibitor p16.

4. The method according to claim 1 or 2, wherein the overexpression is determined by detecting the cyclin-dependent kinase inhibitor p16.

5. The method according to claim 4, comprising reacting an antibody directed against the cyclin-dependent kinase inhibitor p16 with the body sample.

* * * * *